(12) United States Patent
Cao et al.

(10) Patent No.: US 8,219,229 B2
(45) Date of Patent: Jul. 10, 2012

(54) VIRTUAL HEART VALVE

(75) Inventors: Hengchu Cao, Irvine, CA (US); Wei Sun, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1346 days.

(21) Appl. No.: 11/680,519

(22) Filed: Feb. 28, 2007

(65) Prior Publication Data

US 2007/0208550 A1      Sep. 6, 2007

Related U.S. Application Data

(60) Provisional application No. 60/778,322, filed on Mar. 2, 2006.

(51) Int. Cl.
*G06F 19/00* (2006.01)
(52) U.S. Cl. .......................................... 700/98; 700/118
(58) Field of Classification Search .................... 700/98, 700/118
See application file for complete search history.

(56) References Cited

U.S. PATENT DOCUMENTS

| | | | |
|---|---|---|---|
| 4,364,127 A | 12/1982 | Pierce et al. | |
| 4,731,074 A * | 3/1988 | Rousseau et al. | 623/2.19 |
| 5,961,549 A * | 10/1999 | Nguyen et al. | 623/2.12 |
| 6,165,215 A * | 12/2000 | Rottenberg et al. | 623/2.12 |
| 6,245,105 B1 * | 6/2001 | Nguyen et al. | 623/2.13 |
| 6,328,763 B1 * | 12/2001 | Love et al. | 623/2.15 |
| 6,413,275 B1 * | 7/2002 | Nguyen et al. | 623/2.13 |
| 6,673,109 B2 * | 1/2004 | Cox | 623/2.12 |
| 6,719,789 B2 * | 4/2004 | Cox | 623/2.13 |
| 6,736,846 B2 * | 5/2004 | Cox | 623/2.12 |
| 6,837,902 B2 * | 1/2005 | Nguyen et al. | 623/2.13 |
| 7,137,184 B2 * | 11/2006 | Schreck | 29/447 |
| 2002/0138137 A1 * | 9/2002 | Cox | 623/2.13 |
| 2003/0074059 A1 * | 4/2003 | Nguyen et al. | 623/2.13 |
| 2003/0097175 A1 * | 5/2003 | O'Connor et al. | 623/2.17 |
| 2004/0078950 A1 * | 4/2004 | Schreck | 29/447 |
| 2004/0082991 A1 * | 4/2004 | Nguyen et al. | 623/2.14 |
| 2004/0088045 A1 * | 5/2004 | Cox | 623/2.13 |
| 2005/0150775 A1 * | 7/2005 | Zhang et al. | 205/640 |

FOREIGN PATENT DOCUMENTS

WO      WO 01/41679      6/2001

(Continued)

OTHER PUBLICATIONS

Borrero, et al., Mechanics of Prosthetic Heart Valves, Applications of Engineering Mechanics in Medicine, GED-University of Puerto Rico, Mayaguez, Dec. 2003.

(Continued)

*Primary Examiner* — Albert Decady
*Assistant Examiner* — Anthony Whittington
(74) *Attorney, Agent, or Firm* — AnneMarie Kaiser; Guy Cumberbatch

(57) ABSTRACT

A computational technique to construct a 3-D valve leaflet geometry. The invention pertains to methodology to construct a 3-D heart valve leaflet geometry using finite element analysis (FEA) to simulate the manual assembly process or, in other words, provide a virtual assembly process as an input to a subsequent simulated valve testing step. The simulated valves may be subjected to simulated cyclic valve opening and closings and the stress levels induced therein monitored. Simulated valve designs with lower principal stresses can then be selected for prototyping. Proposed valves can be subjected to cyclic fatigue stress testing under simulated physiologic conditions to study valve durability.

20 Claims, 8 Drawing Sheets

FOREIGN PATENT DOCUMENTS

WO     WO 02/100301     12/2002

OTHER PUBLICATIONS

Hashim, et al., Interactive Cardio Vascular and Thoracic Surgery: Finite Element Method in Cardiac Surgery, Interactive CardioVascular and Thoracic Surgery 5 (2006), pp. 5-8.

International Search Report for Patent Application No. PCT/US2007/005463, Filed Jan. 3, 2007; mailed Jun. 11, 2007.

International Search Report for Patent Application No. PCT/US2007/005463, Filed Jan. 3, 2007; mailed Jan. 18, 2008.

Lee, et al., Reconstruction of Trileaflet Heart Valve Leaflet Motion by Using Photogrammetry and Biquintic Finite Element Method, Biomedical Engineering Research Institute Florida International University Miami Florida, 2003 Summer Bioengineering Conference, Jun. 25-29, Sonesta Beach, Florida.

Sun et al., Simulated Bioprosthetic Heart Valve Deformation Under Quasi-Static Loading, Journal of Biomechanical Engineering, Nov. 2005, vol. 127, pp. 905-914.

\* cited by examiner

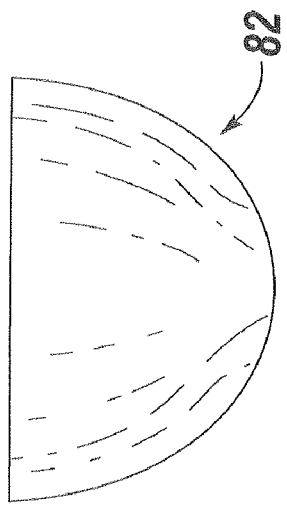
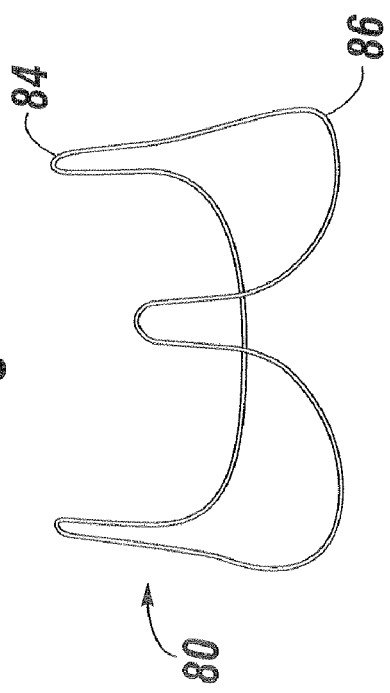
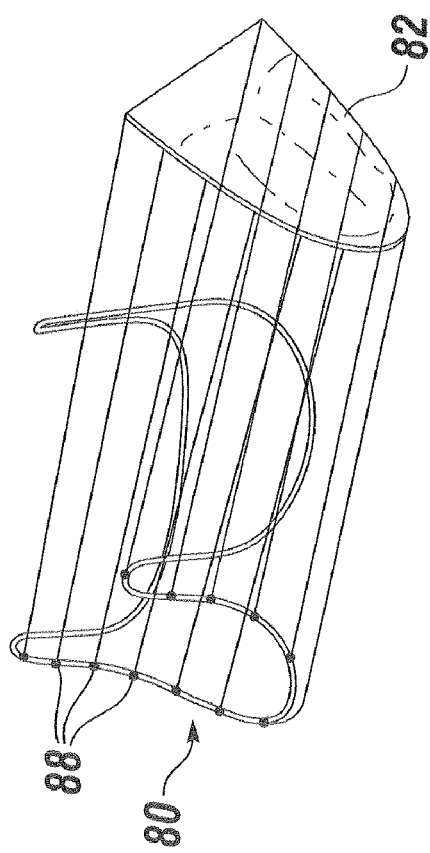

VIRTUAL HEART VALVE

RELATED APPLICATIONS(S)

The present application claims priority under 35 U.S.C. §119(e) to U.S. Provisional Application No. 60/778,322, filed Mar. 2, 2006.

FIELD OF THE INVENTION

The present invention relates to methods and software for simulating a prosthetic heart valve and the dynamic forces applied thereto for the purpose of generating new and improved designs.

BACKGROUND OF THE INVENTION

Heart valve disease continues to be a significant cause of morbidity and mortality, resulting from a number of ailments including rheumatic fever and birth defects. Currently, the primary treatment of aortic valve disease is valve replacement. Recent statistics show that valvular heart disease is responsible for nearly 20,000 deaths each year in the United States, and is a contributing factor in approximately 42,000 deaths. Worldwide, approximately 300,000 heart valve replacement surgeries are performed annually, and about one-half of these patients received so-called mechanical heart valves, which are composed of rigid, synthetic materials. The remaining patients received bioprosthetic heart valve replacements, which utilize biologically derived tissues for flexible fluid occluding leaflets. In general, bioprosthetic valve replacements have good hemodynamic performance and do not require the anticoagulation therapy necessary for mechanical heart valves. However, these bioprostheses sometimes fail as a result of calcification and mechanical damage.

Finite element analysis (FEA) is a computer simulation technique used to study and predict native and prosthetic valve mechanics. FEA uses a numerical technique called the finite element method (FEM). In its application, the object or system is represented by a geometrically similar model consisting of multiple, linked, simplified representations of discrete regions—i.e., finite elements. Equations of equilibrium, in conjunction with applicable physical considerations such as compatibility and constitutive relations, are applied to each element, and a system of simultaneous equations is constructed. The system of equations is solved for unknown values using the techniques of linear algebra or nonlinear numerical schemes, as appropriate. While being an approximate method, the accuracy of the FEA method can be improved by refining the mesh in the model using more elements and nodes.

Particular challenges are encountered in numerical simulations of bioprosthetic heart valves, including nonlinear anisotropic leaflet mechanical properties, leaflet contact, and experimental validation. In particular, experimental measurements of leaflet strain for validation are difficult to perform because of practical limitations in obtaining measurements very close to the leaflets and valve housing. Moreover, prior design models are based on empirical methods of obtaining the leaflet geometry, which is difficult due to the free-form shape of the valve leaflets. Physical measurements of an actual valve using, for example, a Coordinate Measuring Machine (CMM) or optical imager is cumbersome and prone to systemic in human errors, thus prohibiting efficient design evaluations. Furthermore, because of an imprecise knowledge of surface definitions, computer-aided design (CAD) tools can only approximate valve leaflets surfaces, and important design features may be lost.

In view of drawbacks associated with previously known techniques for modeling bioprosthetic heart valves, a more accurate and flexible method is desired.

SUMMARY OF THE INVENTION

The present invention provides a computational technique (i.e., software) to reconstruct a 3-D valve leaflet geometry. The invention pertains to methodology to construct a 3-D heart valve leaflet geometry rising finite element analysis (FEA) to simulate the manual assembly process or, in other words, provide a virtual assembly process as an input to a subsequent simulated valve testing step.

The present invention utilizes computational methods to generate a 3-D bioprosthetic heart valve geometry. Starting from the drawing of a leaflet in flat form, a 3-D valve model is virtually created by simulating the valve assembly process in which the flat form leaflet is wrapped and mounted to the valve wireframe. The virtual assembly technique allows the precise determination of the 3-D geometry of the leaflets based on the leaflet flat pattern and the 3-D wireform assembly process. This technique enables designers to rapidly prototype valves with different leaflet and/or stent designs and to perform stress analysis before physical builds One aspect of the invention is a method of modeling a prosthetic heart valve with a computer program, including first entering two-dimensional geometry and material parameters of a flexible heart valve leaflet into a finite element analysis program to define a simulated leaflet. The three-dimensional geometry and material parameters of a heart valve support frame are also entered into the finite element analysis program to define a simulated support frame. Then, the program derives the topography of a plurality of the simulated leaflets in three dimensions by imposing edge constraints on the simulated leaflets at their intersections with the support frame. In essence, the program arranges a plurality of the simulated leaflets in three dimensions within the simulated support frame, and imposes edge constraints on the simulated leaflets at their intersections with the support frame.

In one simulated valve, the support frame is generally tubular, wherein the plurality of leaflets are arranged generally in a tube within the support frame. The edge constraints may comprise a continuous line fixing the tube of leaflets around an inflow end of the support frame, and a plurality of generally axial lines located at the intersections of adjacent axial edges of the leaflets. The edge constraints desirably further include rotational constraints at the intersection of adjacent axial edges of the leaflets such that they extend radially outward and parallel to each other. In one embodiment, the edge constraints further include forces that displace discrete points along the adjacent axial edges of the leaflets outwards and constrain the three translational degrees of freedom of the discrete points. This technique mimics individual suture stitches. One simulation involves displacing outward inflow portions of the adjacent axial edges of the leaflets until they intersect the support frame, and displacing outflow portions outward but spacing them from the support frame.

In an alternative simulated valve, the support frame defines an undulating continuous line with upstanding outflow commissures and arcuate inflow cusps therebetween, wherein each leaflet is arranged generally around an arcuate cusp with the edge constraints imposed along the cusps. Desirably, the edge constraints include forces that displace discrete points on the leaflets outward until they intersect the support frame, the forces constraining the three translational degrees of freedom of the discrete points, thus mimicking individual suture stitches.

The material parameters of the simulated leaflets may be modeled elastomeric polymer thin sheet characterized by a nonlinear hyperelastic property, or may be modeled polymer thin sheet approximated by a linear elastic property. In one specific example, the material parameters of the flexible heart valve leaflets are modeled biological tissues characterized by a nonlinear, anisotropic Fung type tissue model, within which the second Piola-kirchhoff stress S can be derived from a strain energy function W through:

$$S = \frac{\partial W}{\partial E} \quad (1)$$

where E is the Green strain tensor, and wherein
a Fung elastic model is utilized with full expansion of quadric terms of Q and with the ability to characterize in-plane shear response:

$$W = \frac{c}{2}[e^Q - 1] \quad (2)$$
$$Q = A_1 E_{11}^2 + A_2 E_{22}^2 + 2A_3 E_{11} E_{22} + A_4 E_{12}^2 + 2A_5 E_{12} E_{11} + 2A_6 E_{12} E_{22}$$

where c and $A_i$ are material constants.

Another aspect of the invention is a method of testing a simulated prosthetic heart valve. Firsts the method provides a two-dimensional drawing of a simulated heart valve leaflet having a cusp edge and a free edge. A simulated valve assembly procedure forms a simulated heart valve by attaching the cusp edge of a plurality of the leaflets to a simulated 3-dimensional heart valve support frame using finite element analysis software, and applying edge constraints at the support frame to the cusp edges. Nonlinear tissue material constitutive properties are applied in the finite element analysis software. The method applies simulated valve opening and closing fluid cycles to the simulated heart valve, and simulated stresses induced in the simulated heart valve by the application of simulated valve opening and closing cycles are monitored. The method desirably includes subjecting the simulated heart valve to cyclic fatigue stress testing under simulated physiologic conditions to study valve durability.

Another aspect of the invention is a method of selecting a prosthetic heart valve design for prototyping. First, the method provides a two-dimensional drawing of a simulated heart valve leaflet having a cusp edge and a free edge. A simulated valve assembly procedure forms a simulated heart valve by attaching the cusp edge of a plurality of the leaflets to a simulated 3-dimensional heart valve support frame using finite element analysis software, and imposing edge constraints on the leaflets at their intersections with the support frame. Nonlinear tissue material constitutive properties are applied in the finite element analysis software. The method applies simulated valve opening and closing fluid cycles to the simulated heart valve, and obtains a stress distribution in the leaflets. The preceding steps are performed for at least two simulated heart valves, and a prototypical valve then built based on a comparison of the observed stress distribution in the leaflets of the simulated valves. For instance, the prototypical valve built may be based on the simulated valve in which the lowest principal stresses in the leaflets throughout the opening and closing cycles are observed.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

Features and advantages of the present invention will become appreciated as the same become better understood with reference to the specification, claims, and appended drawings wherein:

FIGS. 9A-9C are images of components of an alternative heart valve simulated in accordance with the methods of the present invention summit.

DETAILED DESCRIPTION OF THE PREFERRED EMBODIMENTS

Figure 1A:
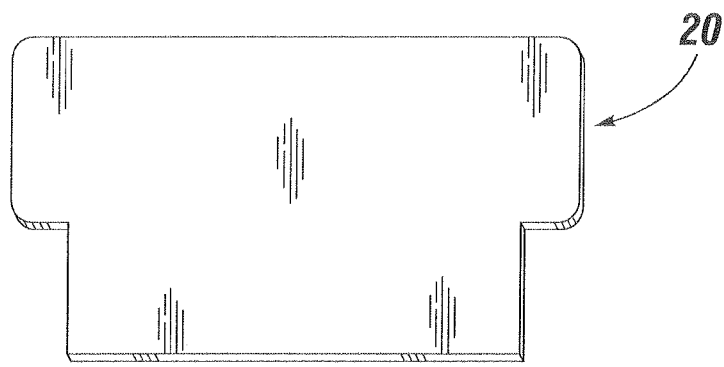
FIG. 1A is a flat plan view of an exemplary heart valve leaflet which is modeled by the methods of the present invention.

The present invention is an improved software-based technique for constructing a virtual three-dimensional heart valve. Such a virtual heart valve is useful for testing purposes prior to prototype or development model build. In particular, the methods described herein are desirably performed between the design and prototype stages. An accurate model for simulating heart valves and their operation in three dimensions is an extremely valuable tool for experimental purposes. At present, there is a great deal of interest in new collapsible much expandable heart valves that are delivered via minimally-invasive surgical or percutaneous approaches. However, this effort involves the design of new heart valve geometries that have not been clinically proven. Therefore, a computational model that produces an accurate virtual heart valve and can simulate dynamic conditions saves a great amount of time and money.

Performance of stress analysis and evaluation of flexible leaflet valve designs generally requires three components: leaflet material properties, valve geometry and valve loading conditions.

The first of these has proved to be a very difficult subject of study. Flexible leaflets used in heart valves are typically made from bioprosthetic homograft or xenograft materials. For example, the most successful bioprosthetic materials are whole porcine valves and separate leaflets made from bovine pericardium stitched together to form a tri-leaflet valve. In addition, flexible leaflets formed of polymeric materials have been proposed, though they have not yet proven successful in practice. The mechanical and dynamic properties of even well-known polymeric materials formed into heart valve leaflets are difficult to predict, and the properties of bioprosthetic leaflets even more so. One survey paper in this area is provided by Borrero, et al., in "Mechanics of Prosthetic Heart Valves," Applications of Engineering Mechanics in Medicine, GED—University of Puerto Rico, Muyaguez (2003).

Despite the difficulties, a number of researchers have undertaken the task of quantifying flexible leaflet properties. The technique of finite element analysis (FEA) has often been applied to the problem of predicting flexible leaflet properties. For example, Sun, et al., "Simulated Bioprosthetic Heart Valve Deformation under Quasi-static Loading," Journal of Biomechanical Engineering, Volume 127, pp. 905-914, November, 2005, extensively describes previous work in FEA of native and prosthetic heart valves.

In accordance with one technique, the material parameters of the flexible heart valve leaflets are modeled elastomeric polymer thin sheet characterized by a nonlinear hyperelastic property, such as Mooney Rivlin and Ogden models. Alternatively, the material parameters of the flexible heart valve leaflets are modeled polymer thin sheet approximated by a linear elastic property, such as Young's modulus and Poisson's ratio.

Sun, et al. provide a particularly useful approximation of the properties of bioprosthetic tissue, in particular modeling bovine pericardial tissue. First, the leaflet material properties are experimentally measured and accurately characterized by the nonlinear, anisotropic Fung type tissue model. Briefly, it was assumed that biological tissues behave as hyperelastic materials following the concept of pseudo-elasticity (Fung, Y. C., Biomechanics: Mechanical Properties of Living Tissues. 2nd ed. 1993, New York: Springer Verlag. 568). Thus, the second Piola-kirchhoff stress S can be derived from a strain energy function W through:

$$S = \frac{\partial W}{\partial E} \quad (1)$$

where E is the Green strain tensor. A Fung elastic model is desirably utilized with full expansion of quadric terms of Q and with the ability to characterize in-plane shear response:

$$W = \frac{c}{2}[e^Q - 1] \quad (2)$$
$$Q = A_1 E_{11}^2 + A_2 E_{22}^2 + 2A_3 E_{11} E_{22} + A_4 E_{12}^2 + 2A_5 E_{12} E_{11} + 2A_6 E_{12} E_{22}$$

where c and $A_i$ are material constants. For instance, the parameters for the chemically (glutaraldehyde) treated bovine pericardium (GLBP) for the leaflet are listed in Table 1 (Sun, W. and M. S. Sacks, Finite Element Implementation of a Generalized Fung-Elastic Constitutive Model for Planar Tissues. Biomechanics and Modeling in Mechanobiology, August 2005.)

TABLE 1

Parameter estimates for the three leaflets, fitted with eqn. (2).

| | Parameters | | | | | |
|---|---|---|---|---|---|---|
| c (kPa) | A1 | A2 | A3 | A4 | A5 | A6 |
| Leaflet 5.12 | 60.124 | 86.33 | 2.00 | 203.16 | 43.05 | 42.13 |

The technique has been used to investigate the valve leaflet geometries generated using different material models. The material constants of Polymer, Nitinol and tissue are listed in Table 2. It can be observed that with different material models, geometries of the leaflets are formed very differently.

TABLE 2

Material constants for different material models.

| Material | Elastic Modulus (MPa) | Poisson Ratio | Thickness (mm) |
|---|---|---|---|
| ElastEon | 45.0 | 0.3 | 0.254 |
| Nitinol | 70000.0 | 0.3 | 0.008 |
| Tissue | Table 1 | | 0.4 |

Another required component for stress analysis and evaluation of flexible leaflet valve designs is valve geometry. Again, the present invention is believed to more faithfully simulate bioprosthetic heart valves by essentially constructing the valve within the model. The present invention provides a new method for defining the geometry of a three-dimensional bioprosthetic heart valve for input into the modeling program. In particular, the invention involves simulating the heart valve assembly process in which, starting from the drawing of a leaflet in flat form, a 3-D valve model is virtually created by simulating the valve assembly process in which the flat form leaflet is wrapped and mounted to the valve wireframe.

Figure 1C:
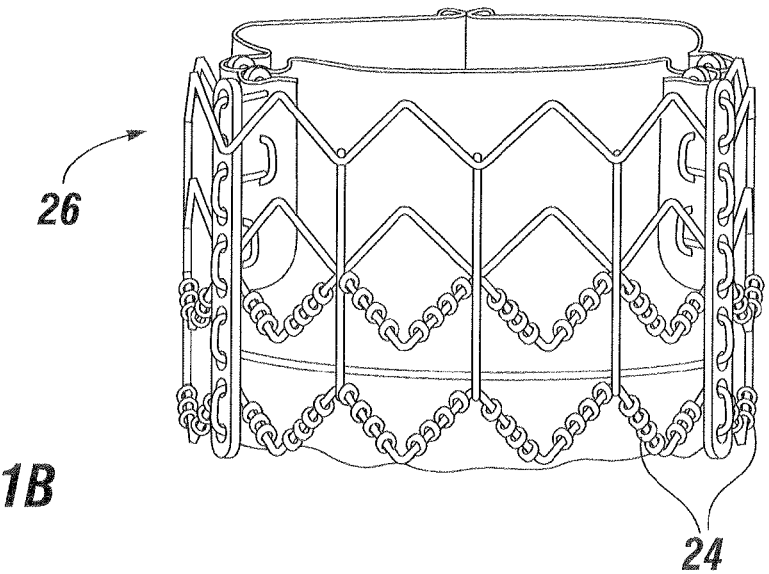
FIG. 1C is a perspective view of an exemplary heart valve which is formed by a simulated heart valve construction of the present invention.
Figure 1B:
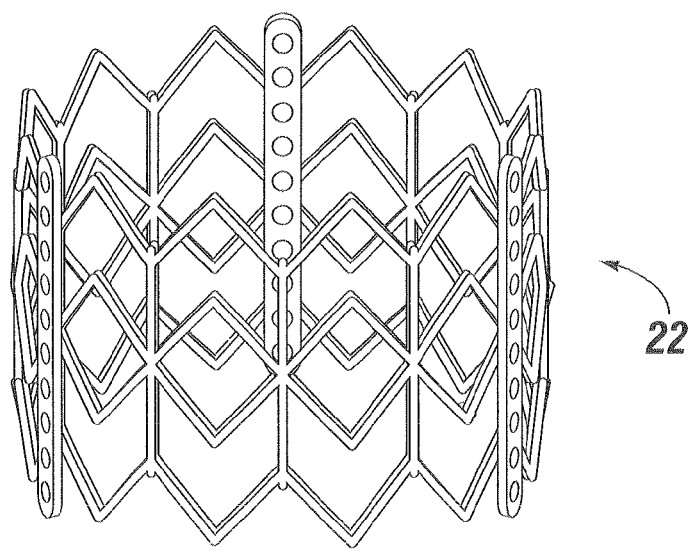
FIG. 1B is a perspective view of an exemplary heart valve support frame which is modeled by the methods of the present invention.

In an actual manufacturing facility, a valve assembler needs a flat pericardium tissue 20 cut according to specification, such as in FIG. 1A, and a valve support frame or stent 22 such as in FIG. 1B. The assembler applies multiple stitches 24 to suture the tissue 20 onto the stent 22 according to specification, and forms an assembled heart valve 26, as showed in FIG. 1C. The particular heart valve shown is an Apogee minimally invasive heart valve available from Edwards Life-Sciences of Irvine, Calif., although the technique may be applied to other valves, such as the Cribier-Edwards Percutaneous Heart Valve.

To mimic the valve assembly process, the finite element model is desirably simplified to permit a solution for the deformations to be found using often limited computational resources, and yet still have sufficient details for it to be an acceptable representation of the real problem. In this approach, for the above mentioned Edwards Apogee minimally invasive heart valve, the simplifications include: the stent was modeled as cylindrical tube, the zigzag geometry of the stent has little impact to the formation of the leaflet geometry. Cloth was not modeled. The leaflet was modeled without the two ears. More or less simplifications may be utilized as desired.

Figure 2B:
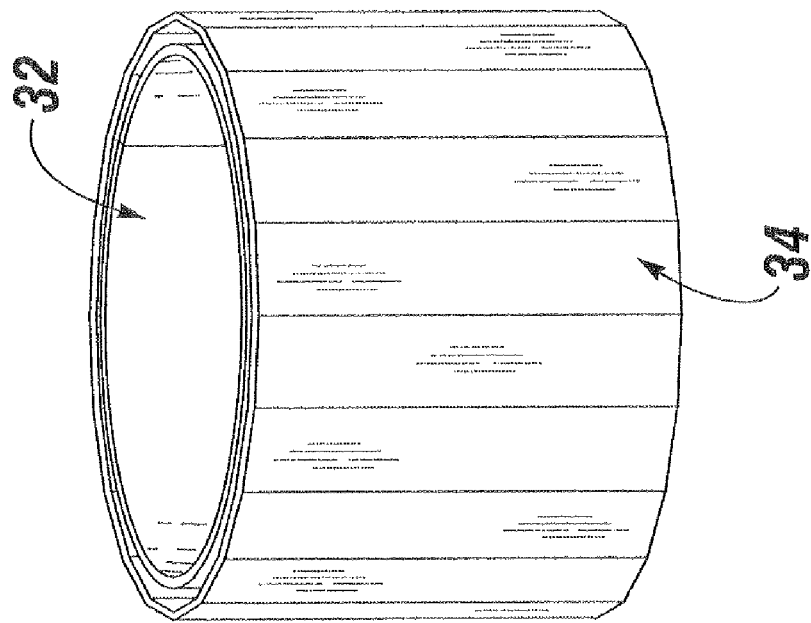
FIG. 2B illustrates an approximation of a heart valve support frame surrounding the conical tube leaflets.
Figure 2A:
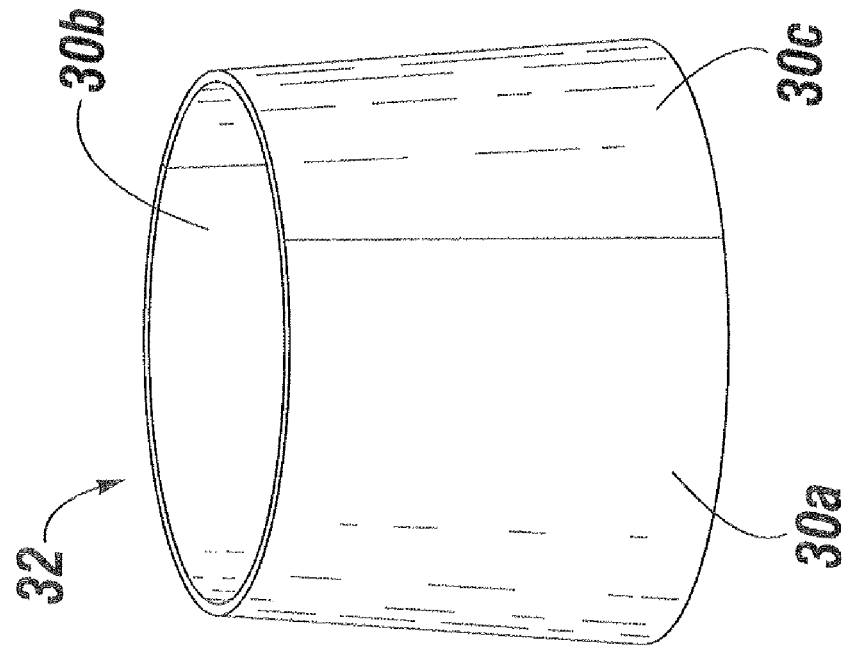
FIG. 2A illustrates an initial geometry of three simulated heart valve leaflets formed into a conical tube in accordance with the present invention.

FIGS. 2A and 2B illustrates key steps for reconstructing an Apogee valve 3D leaflet geometry. First, the stent and leaflet geometry in flat form are obtained from engineering design drawings. Using commercial finite element analysis software ABAQUS (Pawtucket, R.I.), three leaflets 30a, 30b, 30c were virtually joined together to form a cone shape 32 (FIG. 2A) with a smaller upper diameter (e.g., 19.5 mm) and a larger lower diameter (e.g., 21.5 mm). In this sense, the upper end of the leaflets corresponds to the outflow end of the valve. A representative tubular stent 34 with a diameter slightly larger than the cone 32 (e.g., 22 mm) was also virtually generated, as depicted in FIG. 2B.

ABAQUS is an exemplary commercial software package for finite element analysis used in the present technique. Its elastomer (rubberlike) material capabilities are excellent. A material user subroutine is implemented in the ABAQUS framework to provide more accurate description of the deformation behavior of the bovine pericardial tissue material. It has a good general purpose analysis component, ABAQUS/Standard, and a dynamics component, ABAQUS/Explicit. ABAQUS/CAE and ABAQUS/Viewer are the pre- and post-processors for the finite element models. ABAQUS/CAE and ABAQUS/Viewer use the open-source scripting language Python for programmability. Of course, other software for finite element analysis may be used.

Figure 3A:
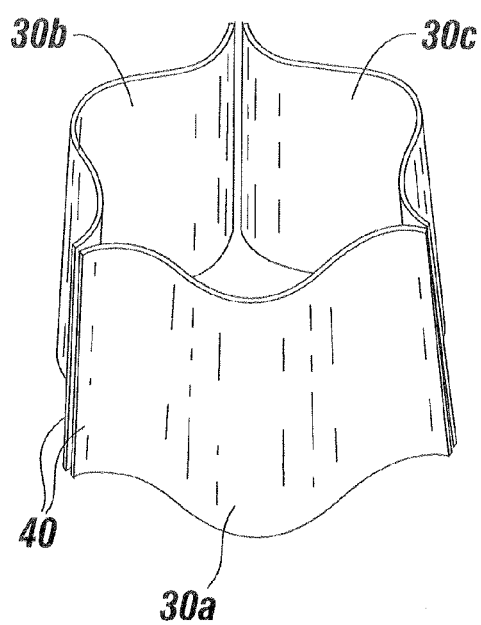
FIGS. 3A and 3B are perspective and top plan views, respectively, of three simulated heart valve leaflets after imposition of a first edge constraint.
Figure 3B:
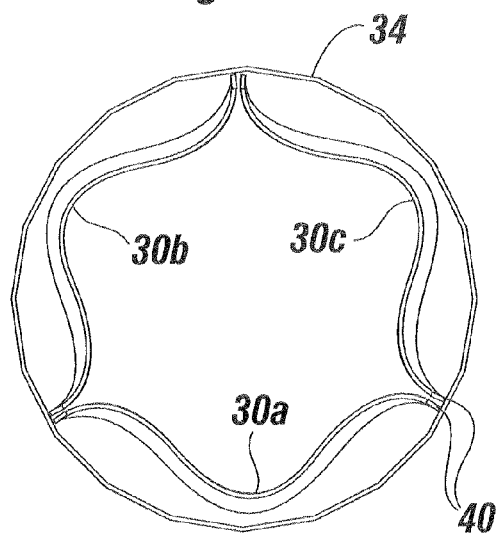

The next step in the virtual heart valve assembly process is to simulate the operation of suturing individual leaflets to the virtual stent. First, as seen in FIGS. 3A and 3B, the vertical edges 40 of the leaflets 30a, 30b, 30c are rotated and tangential constraints enforced such that the two adjunct edges of adjacent leaflets are parallel to each other, mimicking the relative sutured positions of the two leaflets. In other words, the adjacent vertical edges 40 are rotated to extend in parallel radially outward. "Vertical" corresponds to the axial direction parallel to blood flow through the valve.

Figure 4A:
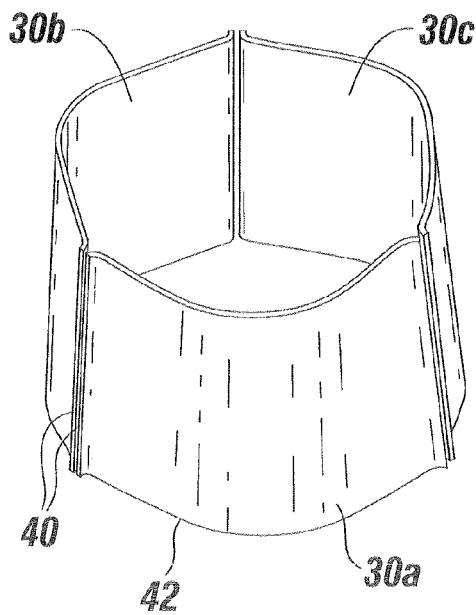
FIGS. 4A and 4B are perspective and top plan views, respectively, of three simulated heart valve leaflets after imposition of a second edge constraint.
Figure 4B:
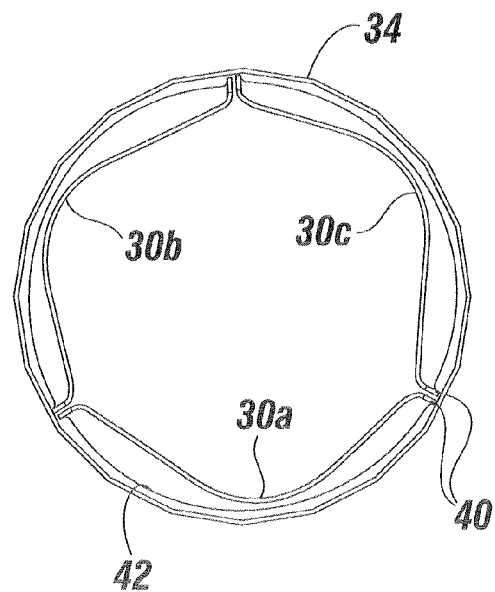

In the actual valve, sutures are used to stitch the leaflets to the stent. The stitching operation is simulated by applying edge constraints or node forces on a plurality, preferably 12, of discrete evenly spaced suture attachment points along each vertical leaflet edge 40. These node forces push the adjacent axial edges 40 of the leaflets 30 outwards until they are in the contact with the stent 34. The three translational degrees of freedom of the nodes are then fixed in the model, mimicking the stitch attachments. A similar operation is performed on the bottom of the leaflet skirt 42 such that the bottom of each virtual leaflet is sutured around the inflow end of the virtual stent, as showed in FIGS. 4A and 4B. At this point, the virtual valve is substantially complete with three leaflets "sutured" around the inflow end of the stent and up along three commissures. By omitting external constraints (as opposed to within the simulated leaflets, or inter-nodal constraints) to movement of all points/nodes that are not fixed to the stent, simulated flow will cause the leaflets to billow inward and outward, thus functioning as a simulated valve. In other words, using FEA to impose edge constraints on the simulated leaflets at their intersections with the support frame (e.g., simulated suture points) permits the derivation of the static topography of a plurality of the simulated leaflets in three dimensions, and then application of simulated flow, in conjunction with material properties, results in an understanding of the dynamic topography and stress distribution.

Figure 5A:
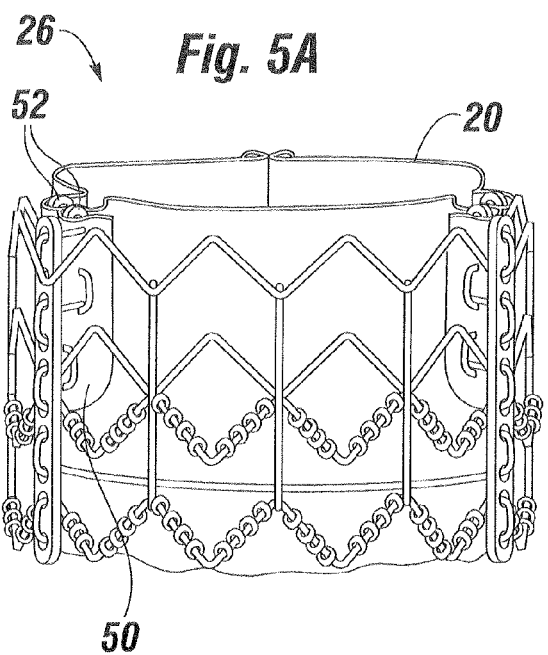
FIGS. 5A and 5B are perspective and top plan views, respectively, of three simulated heart valve leaflets after imposition of a third edge constraint.
Figure 6A:
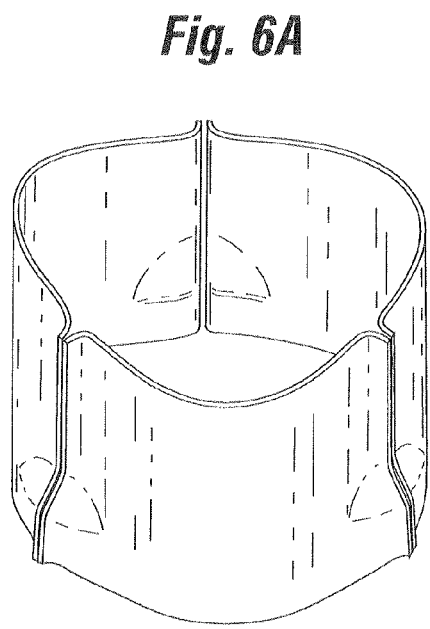
FIGS. 6A and 6B are perspective and top plan views, respectively, of the heart valve of FIG. 1C showing the actual construction upon which the simulated heart valve is modeled.
Figure 5B:
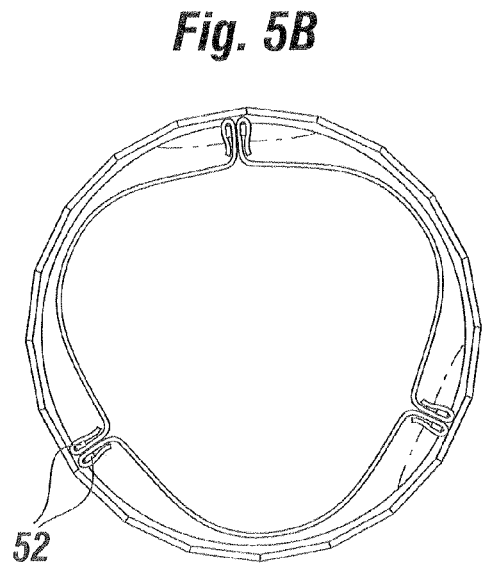
Figure 6B:
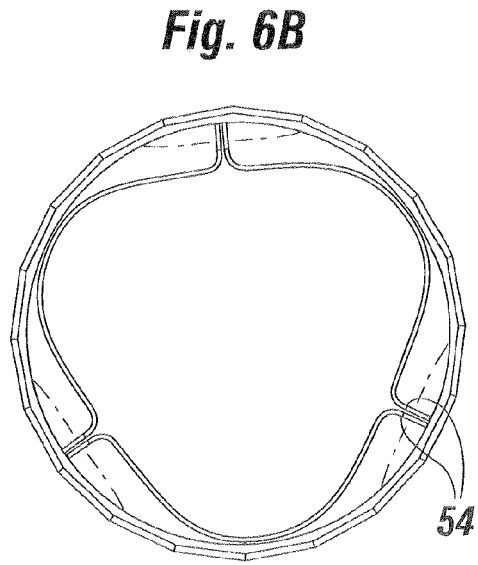

FIGS. 5A-5B and 6A-6B illustrate a refinement to the heart valve model based on the exemplary Edwards Apogee valve being modeled. In particular, FIGS. 5A and 5B show an actual assembled valve 26 with the bovine pericardial leaflets 20 spread outward in the valve open phase. Outer tabs or ears 50 of each of the leaflets wrap around and are sutured to small metallic bars 52 for added reinforcement. Each bar 52 is about 1.5 mm in width and 9 mm in length. Because of the presence of the bars in the commissure regions between the leaflets and the stent, the free edges of the leaflets at those locations are displaced inwards. In a similar manner, the heart valve simulation receives instructions that displace inward the outflow end 54 of the commissures of adjacent leaflets, such as shown in FIGS. 6A and 6B. These points on each of the leaflets remain constrained from movement in their three translational degrees of freedom.

Figure 7:
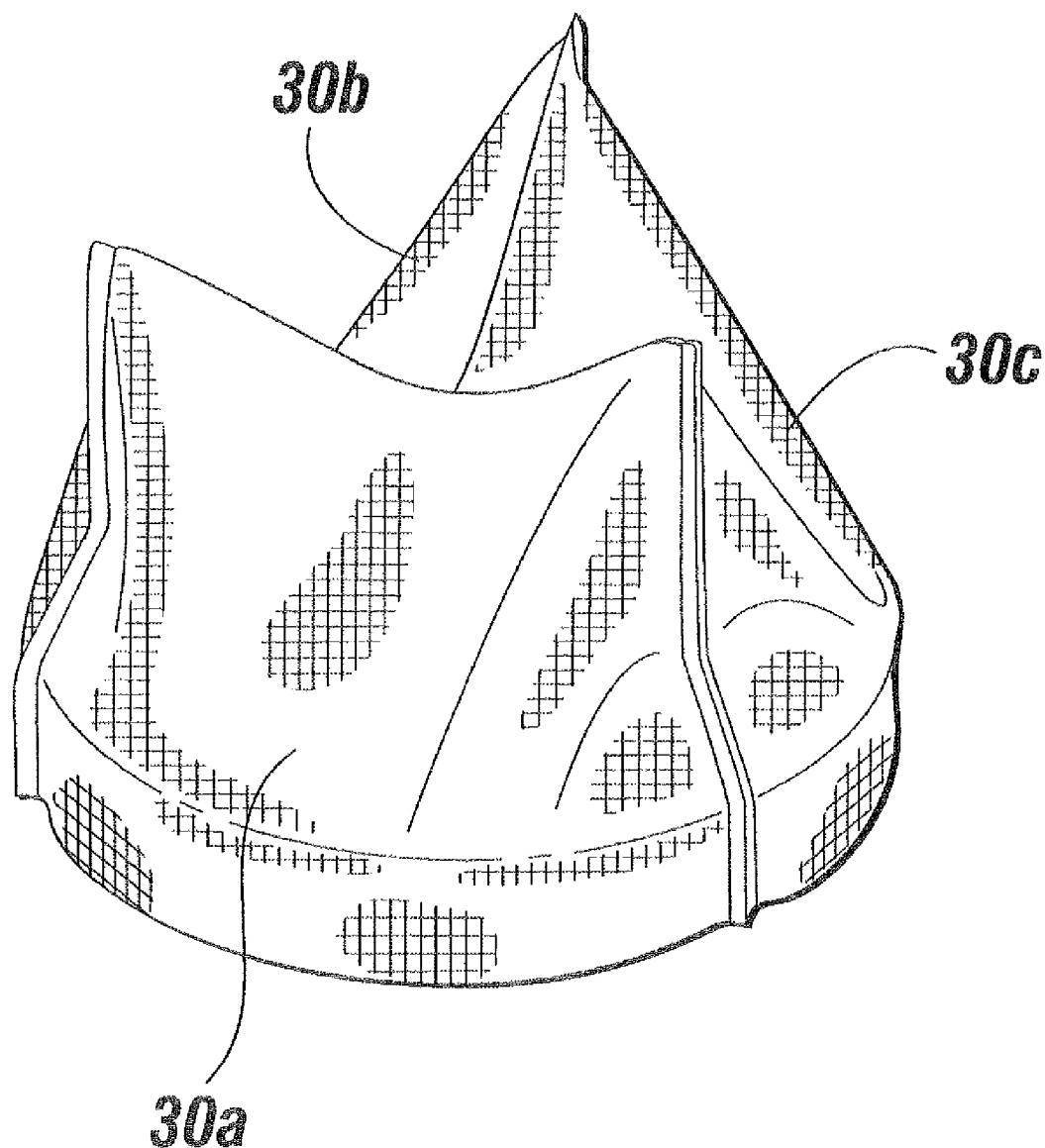
FIG. 7 is a perspective view of the three simulated heart valve leaflets after imposition of edge constraints and after subjected to a simulated fluid closing pressure.

To reach the valve closing geometry, the application of 2 kPa of fluid pressure was simulated on the outflow side of the leaflet surfaces 30a, 30b, 30c. The result in FIG. 7 shows the leaflets of the simulated Apogee valve in their closed positions.

Figure 8C:
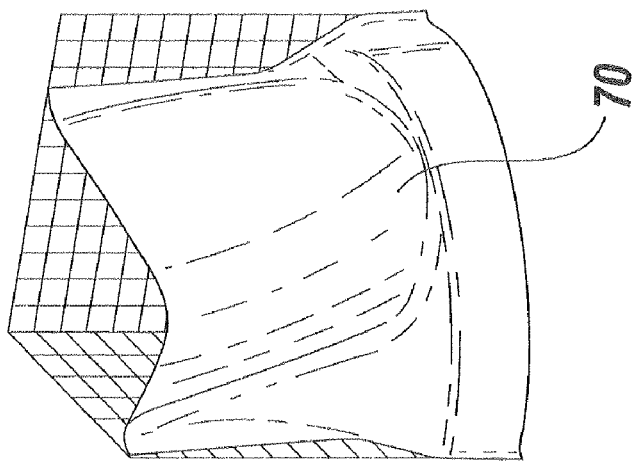
FIGS. 8A-8C are perspective views of individual simulated leaflets having different material properties and after subjected to a simulated fluid closing pressure.
Figure 8B:
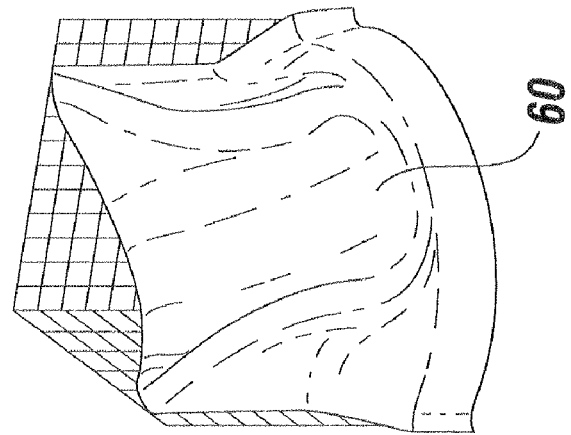
Figure 8A:
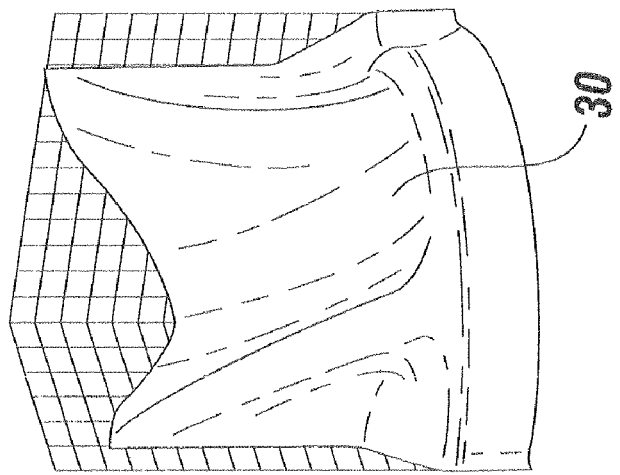

FIGS. 8A-8C illustrate three individual simulated leaflets of different material properties and subjected to the closing pressure described above. FIG. 8A shows the contours of a simulated closed tissue leaflet 30. FIG. 8B is a simulated polymer leaflet 60, and FIG. 8C simulates a Nitinol leaflet 70. These simulations clearly illustrate that with different material models, the responses to fluid pressure of the leaflets are quite different. The more realistic virtual heart valve described herein therefore provides an extremely robust model in which to incorporate and test a wide variety of different materials. Ultimately, the simulations can be used to predict areas of high stress or fatigue/failure for various materials. Desirably, the simulated heart valves are subjected to cyclic fatigue stress (desirably, millions of simulated valve opening and closing fluid cycles) under simulated physiologic conditions to study valve durability.

With reference now to FIGS. 9A-9C, several images of an alternative simulated valve created by software of the present invention are shown. The valve illustrated is of a more conventional, non-expandable variety that in the real world is typically implanted by an open heart surgical procedure. The techniques for simulating this conventional heart valve are similar to those described above for simulating an expandable heart valve, in that simulation involves the construction of the valve to more accurately define the constraints on the flexible leaflets. Although the design of conventional heart valves is relatively mature, there remains room for improvement and the simulation described herein provides an excellent tool for testing different geometries and materials.

FIG. 9A illustrates a simulated stent or support frame 80 (sometimes known as a wireform), while FIG. 9B shows an individual leaflet 82 laid out flat in plan view. The superposition of the leaflet 82 on the support frame 80 is shown in FIG. 9C. The simulation is obviously only partially imaged, and the finished valve will have three leaflets and possibly some other structures simulated, such as a sewing ring surrounding an inflow end.

The support frame 80 defines an undulating continuous line with upstanding outflow commissures 84 and arcuate inflow cusps 86 therebetween. The support frame lies generally in a tubular surface, but often the circle connecting the tips of the commissures is smaller than the circle connecting the lower apices of the cusps so that the support frame defines a conical surface. The support frame in actual commercial heart valves is made of a variety of materials, including biocompatible metal and polymers. Of course, the simulation accommodates essentially an infinite variety of materials.

A plurality of nodes or points 88 around the support frame are drawn to illustrate points at which individual stitches of sutures are used in the real world to connect the flexible leaflets to the stent. Actually, in the real world the stent is usually covered by fabric and the leaflets connected with sutures to the fabric, but the simulation permits the leaflets to be virtually attached directly to the stent.

As with the earlier-described embodiment, each virtual leaflet possesses particular material properties and is described by a plurality of finite elements. FIG. 9C shows the points around the support frame that connect to nodes or points around a cusp edge of the leaflet. In other words, the points around the cusp edge of the leaflet are constrained from movement in their three translational degrees of freedom. The top or free edge of the leaflet remains unconstrained and permits the leaflet to flex in and out in the simulation.

Figure 10:
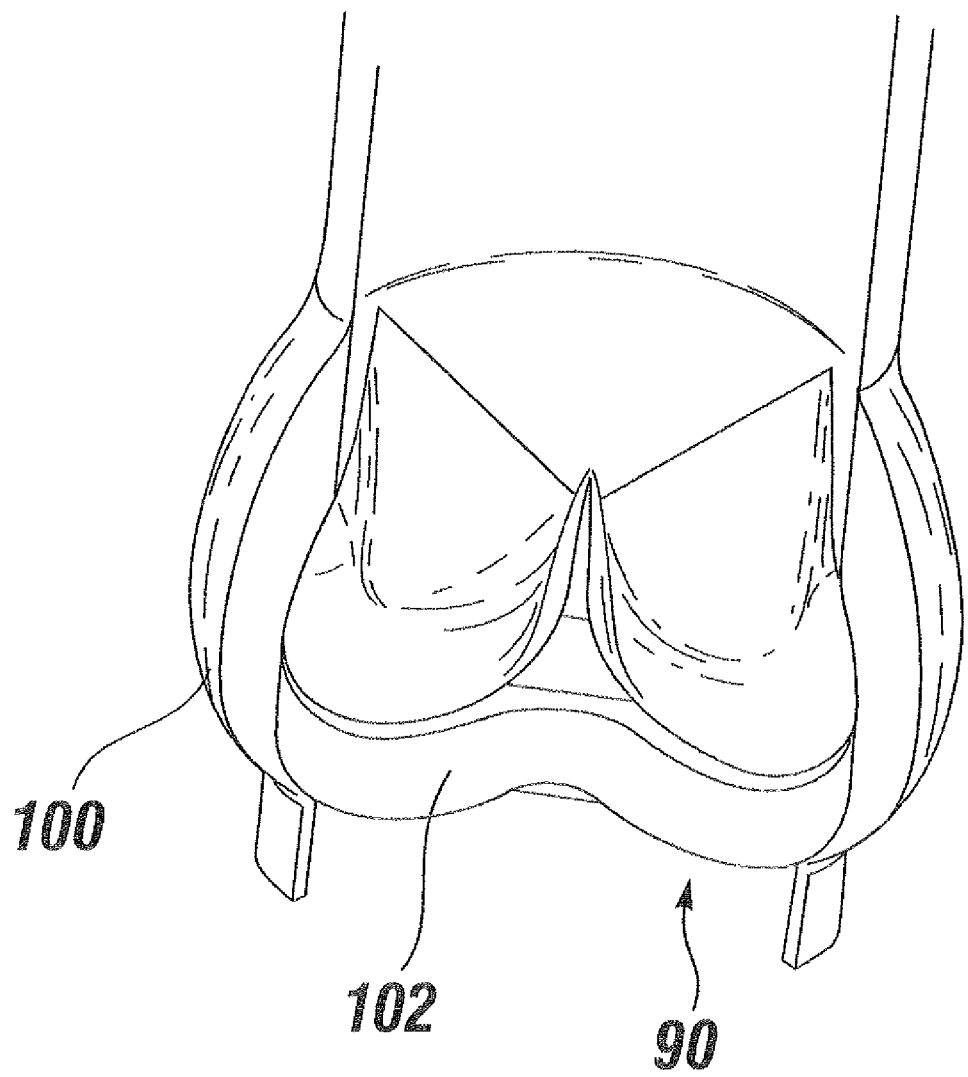
FIG. 10 is an image of an assembled alternative heart valve mounted within a simulated aorta.

FIG. 10 is a perspective view of a virtual heart valve 90 of the present invention positioned within a simulated aorta 100. In this simulation, the heart valve replaces the native aortic valve. The support frame and flexible leaflets are shown, in addition to an interface 102 surrounding the inflow end thereof. The interface 102 simulates a sewing ring used to connect the prosthetic valve to the surrounding tissue.

The material characteristics of the surrounding tissue are provided by any number of known sources. For example, one reference is Ferraresi C. et al., "One-dimensional experimental mechanical characterization of porcine aortic root wall" Medical and Biological Engineering and Computing, Vol 37, 1, 1999: 202-207, which describes the mechanical properties of both natural and chemically fixed porcine aortic wall obtained under a uniaxial testing condition. Ferraresi et al. reported the stress-strain characteristics of fresh and fixed tissue in all zones of the aortic wall, both in circumferential and axial directions. Also, Nicosia M A et al., "Biaxial mechanical properties of porcine ascending aortic wall tissue", J Heart Valve Dis. 2002 September; 11(5):680-6, reported biaxial mechanical properties of the aortic root wall, and found that porcine aortic root wall tissue is an anisotropic material with linear elastic properties for strains up to 40%. Constitutive models used for modeling these material properties in finite element models have been recently discussed in the review paper by Sacks et al, "Bioprosthetic heart valve heterograft biomaterials: structure, mechanical behavior and computational simulation", Expert Rev Med Devices, 2006 November;3(6):817-34.

The simulation of the valve within a vessel shown in FIG. 10 is a precursor to actual construction of a prototypical valve and flow testing within a test fixture (not shown). Fabric coverings and a sewing ring are part of the actual valve, and these components may be included in the simulation but are typically omitted for the sake of expediency and to reduce the amount of required processing memory.

The virtual heart valves whose simulation is described above are extremely useful for both visualizing and testing new prosthetic heart valves. For example, one application of the technology involves providing a two-dimensional drawing of the simulated heart valve leaflet and then simulating a valve assembly procedure. The assembly procedure involves applying boundary conditions to attach all but the free edge of each leaflet to a simulated three-dimensional support frame. Edge constraints are imposed on the leaflets, and nonlinear tissue material constitutive properties are applied thereto. Simulated valve opening and closing pressures are applied to the valve to obtain a stress distribution leaflets. By analyzing the resulting stress distribution, regions of high stress and therefore possible failure can be identified. By incrementally changing the geometry of the two-dimensional leaflets, or modifying the material properties, any number of proposed prosthetic valves can be virtually tested in this manner. The cost savings in terms of eliminating corresponding prototypes is substantial. Only the most promising designs can then be converted into prototypes and the stress distribution tested empirically.

While the invention has been described in its preferred embodiments, it is to be understood that the words which have been used are words of description and not of limitation. Therefore, changes may be made within the appended claims without departing from the true scope of the invention.

What is claimed is:

1. A method of modeling a prosthetic heart valve with a computer program, comprising:
   entering two-dimensional geometry and material parameters of a flexible heart valve leaflet into a finite element analysis program to define a simulated leaflet;
   entering the three-dimensional geometry and material parameters of a heart valve support frame using the finite element analysis program to define a simulated support frame; and
   deriving the topography of a plurality of the simulated leaflets in three dimensions by imposing edge constraints on the simulated leaflets at their intersections with the support frame, wherein
   the simulated support frame is tubular or frusto-conical, wherein the plurality of simulated leaflets are arranged in a tube or frusto-cone within the support frame, and wherein the edge constraints comprise a continuous line fixing the tube or frusto-cone of simulated leaflets around an inflow end of the simulated support frame, and a plurality of generally axial lines located at the intersections of adjacent axial edges of the simulated leaflets.

2. The method of claim 1, wherein the material from which the material parameters of the heart valve support frame are derived is Nitinol.

3. The method of claim 1, wherein the edge constraints further include rotational constraints at the intersection of adjacent axial edges of the simulated leaflets such that the adjacent axial edges extend radially outward and parallel to each other.

4. The method of claim 3, wherein the edge constraints further include forces that displace discrete points along the adjacent axial edges of the simulated leaflets outwards and constrain the three translational degrees of freedom of the discrete points.

5. The method of claim 4, wherein inflow portions of the adjacent axial edges of the simulated leaflets are displaced outward until the inflow portions intersect the simulated support frame, while outflow portions are displaced outward but remain spaced from the simulated support frame.

6. The method of claim 1, wherein the simulated support frame defines an undulating continuous line with upstanding outflow commissures and arcuate inflow cusps therebetween, wherein each simulated leaflet is arranged around an arcuate cusp with the edge constraints imposed along the cusps.

7. The method of claim 6, wherein the edge constraints include forces that displace discrete points on the simulated leaflets outward until the discrete points intersect the simulated support frame, the forces constraining the three translational degrees of freedom of the discrete points.

8. The method of claim 1, wherein the material parameters of the flexible heart valve leaflets are modeled biological tissues characterized by a nonlinear, anisotropic Fung type tissue model, within which the second Piola-kirchhoff stress S can be derived from a strain energy function W through:

$$S = \frac{\partial W}{\partial E} \quad (1)$$

where E is the Green strain tensor, and wherein
a Fung elastic model is utilized with full expansion of quadric terms of Q and with the ability to characterize in-plane shear response:

$$W = \frac{c}{2}[e^Q - 1] \quad (2)$$
$$Q = A_1 E_{11}^2 + A_2 E_{22}^2 + 2A_3 E_{11} E_{22} + A_4 E_{12}^2 + 2A_5 E_{12} E_{11} + 2A_6 E_{12} E_{22}$$

where c and $A_i$ are material constants.

9. The method of claim 1, wherein the material parameters of the simulated leaflets are modeled elastomeric polymer thin sheet characterized by a nonlinear hyperelastic property.

10. The method of claim 1, wherein the material parameters of the simulated leaflets are modeled polymer thin sheet approximated by a linear elastic property.

11. A method of testing a simulated prosthetic heart valve, comprising:
providing a two-dimensional drawing of a simulated heart valve leaflet having a cusp edge and a free edge;
simulating a valve assembly procedure to form a simulated heart valve by attaching the cusp edge of a plurality of the leaflets to a simulated 3-dimensional heart valve support frame using finite element analysis software, and applying edge constraints at the support frame to the cusp edges;
applying nonlinear tissue material constitutive properties in the finite element analysis software;
applying simulated valve opening and closing fluid cycles to the simulated heart valve; and
monitoring simulated stresses induced in the simulated heart valve by the application of simulated valve opening and closing cycles, wherein
the simulated support frame is tubular or frusto-conical, wherein the plurality of simulated leaflets are arranged in a tube or frusto-cone within the support frame, and wherein the edge constraints comprise a continuous line fixing the tube or frusto-cone of simulated leaflets around an inflow end of the simulated support frame and a plurality of generally axial lines located at the intersections of adjacent axial edges of the simulated leaflets.

12. The method of claim 11, wherein the material from which the nonlinear tissue material constitutive properties in the finite element analysis software are derived is bovine pericardial tissue.

13. The method of claim 11, wherein the edge constraints include forces that displace discrete points on the simulated leaflets outward until the discrete points intersect the simulated support frame, the forces constraining the three translational degrees of freedom of the discrete points.

14. The method of claim 11, wherein the simulated support frame defines an undulating continuous line with upstanding outflow commissures and arcuate inflow cusps therebetween, wherein each simulated leaflet is arranged around an arcuate cusp with the edge constraints imposed along the cusps.

15. The method of claim 1, further including subjecting the simulated heart valve to cyclic fatigue stress testing under simulated physiologic conditions to study valve durability.

16. A method of selecting a prosthetic heart valve design for prototyping, comprising:
providing a two-dimensional drawing of a simulated heart valve leaflet having a cusp edge and a free edge;
simulating a valve assembly procedure by attaching the cusp edge of a plurality of the leaflets to a simulated 3-dimensional heart valve support frame using finite element analysis software;
imposing edge constraints on the leaflets at their intersections with the support frame;
applying nonlinear tissue material constitutive properties in the finite element analysis software;
applying simulated valve opening and closing fluid cycles;
obtaining a stress distribution in the leaflets;
performing the steps above for at least two simulated heart valves; and
building a prototypical valve based on a comparison of the observed stress distribution in the leaflets of the simulated valves, wherein
the simulated support frame is tubular or frusto-conical, wherein the plurality of simulated leaflets are arranged in a tube or frusto-cone within the support frame, and wherein the edge constraints comprise a continuous line fixing the tube or frusto-cone of simulated leaflets around an inflow end of the simulated support frame and a plurality of generally axial lines located at the intersections of adjacent axial edges of the simulated leaflets.

17. The method of claim 16, further including:
building a prototypical valve based on the simulated valve in which the lowest principal stresses in the leaflets throughout the opening and closing cycles are observed.

18. The method of claim 16, wherein the material from which the nonlinear tissue material constitutive properties in the finite element analysis software are derived is bovine pericardial tissue.

19. The method of claim 16, wherein the edge constraints include forces that displace discrete points on the simulated leaflets outward until the discrete points intersect the simulated support frame, the forces constraining the three translational degrees of freedom of the discrete points.

20. The method of claim 16, wherein the simulated support frame defines an undulating continuous line with upstanding outflow commissures and arcuate inflow cusps therebetween, wherein each simulated leaflet is arranged around an arcuate cusp with the edge constraints imposed along the cusps.

* * * * *